United States Patent [19]
Coates et al.

[11] Patent Number: 4,680,030
[45] Date of Patent: Jul. 14, 1987

[54] GARMENT HAVING IMPROVED, SELF CLOSING, FILAMENTARY FASTENERS

[76] Inventors: Fredrica V. Coates, 1608 Dublin Rd., Charlottesville, Va. 22903; Richard Jannoni, 16 Whitehall Ave., Edison, N.J. 08820; Jean Orsini, 813 New York Ave., Raritan, N.J. 08869

[21] Appl. No.: 797,806

[22] Filed: Nov. 13, 1985

[51] Int. Cl.$^4$ ............................................. A61F 13/16
[52] U.S. Cl. ................................................... 604/391
[58] Field of Search ............. 604/391, 390, 389, 385.1

[56] References Cited

U.S. PATENT DOCUMENTS 4,537,591 8/1985 Coates ................................. 604/391
4,568,342 2/1986 Davis ................................... 604/391

*Primary Examiner*—John D. Yasko
*Attorney, Agent, or Firm*—Lowe Price LeBlanc Becker & Shur

[57] ABSTRACT

A diaper or other garment comprises a first piece of fluid absorbant fabric (12) profiled to the contour of a human body and having a pair of arcuate corner extensions (20) carrying hook type filamentary fastener strips (26) adapted to be coupled to loop type filamentary material (24) on a stomach portion of the garment when the garment is folded to be worn. An arcuate, protective cover (28) at each corner extension carries a filamentary loop strip (32) to self-close with the filamentary hooks (26) on the extensions and thereby protect the hooks (26) from lint during washing. Each filamentary strip (26, 32) is sewn to a fabric base (35) to prevent the strip from wrinkling or warping as a result of the high temperatures associated with commercial laundering. In another embodiment, a pair of two ply fabric tabs (46, 48) attached together at one end and to a waist belt (56) or garment (37) carry a strips (50, 52) of complementary filamentary fastener material. The strips are centrally positioned and span the width of the tabs whereby when the strips (50, 52) are coupled to each other, the region of the tabs (46, 48) above the strips (50, 52) establishes a loop to receive the end loops of an absorbant pad insert (38).

20 Claims, 20 Drawing Figures

GARMENT HAVING IMPROVED, SELF CLOSING, FILAMENTARY FASTENERS

TECHNICAL FIELD

The invention related generally to adjustable garments having filamentary material type fasteners, and more particularly, toward adjustable protective underwear having filamentary type fasteners that self-close for protection from lint and resist wrinkling during commercial laundering.

BACKGROUND ART

Garments, such as infant and adult diapers, diaper covers, pants, maternity skirts, and the like, having filamentary material type fasteners, such as Velcro, to enable the size of the garment to be adjusted to individual body profiles, have recently been developed. In U.S. Pat. No. 4,475,912, a fabric diaper having a number of filamentary hook and loop fastener strips is adjustable in size by folding to accommodate infant growth. To remove lint from filamentary hooks that tends to accumulate during washing, a comb-like tool is used to manually comb lint away from the filamentary hooks.

To eliminate the necessity to manually remove lint from the filamentary hook fasteners, U.S. Pat. No. 4,475,912, to Frederica V. Coates, provides protective cover strips formed of loop type filamentary type material positioned adjacent each hook type filamentary fastener in face-to-face presentation in such a way that the protective strip and hook type fastener tend to pivot together or "self-close" during washing.

In Application Ser. No. 631,885, filed on July 18, 1984 to Coates, a diaper cover or pants is provided with filamentary hook and loop type fasteners to enable the size of the pants to be altered to accommodate different infant or adult waist and leg sizes. Self-closing filamentary loop protective covers insulate the filamentary hook fasteners during washing. Other applications of self-closing protective covers for filamentary hook fasteners in adjustable size garments are shown in copending applications Ser. No. 733,054 filed May 9, 1985, Ser. No. 733,051 filed May 9, 1985, and Ser. No. 797,807 filed Nov. 13, 1985, continuation-in-part of Ser. No. 631,885 all to Coates and Jannoni.

Although the self-closing protective cover is an effective device for virtually eliminating lint buildup on filamentary hook fasteners in domestic laundering, the fastener strips tend to wrinkle or warp during extended exposure to the higher temperatures and harsher chemicals of commercial laundering.

One object of the invention described herein, therefore, is to provide filamentary hook and loop fasteners that avoid warping and wrinkling and also resist deterioration in a commercial laundering environment as exists in nursing homes, hospitals, diaper services and other institutions.

Another object is to provide self-closing filamentary fasteners that maintain their planar shape and resist deterioration when exposed to high temperatures during washing.

An additional object is to provide a diaper, pants or other garment that uses filamentary hook and loop fasteners to provide size adjustment, wherein the filamentary fasteners are self-protected from lint buildup and avoid wrinkling or warping and deterioration during commercial laundering.

A further object is to provide self-closing filamentary fasteners of the above type, that are easily and economically manufactured, and do not detract from the appearance of a garment.

There also is a growing need for a convenient device to retain protective pad insert to the body of a wearer. The device must be comfortable and unobtrusive when worn, be easy to use, i.e., quickly attachable to and removeable from an absorbant pad, and easily maintained. Filamentary hook and loop fasteners are used conveniently as a coupling device as described in "Pending Application" Ser. No. 631,885, and continuation-in-part of 631,885 to Coates and Janoni, supra. Although satisfactory for disposable absorbant pads, there exists a need to provide a device for the retention of washable absorbant pad inserts. Because the complementary filamentary hook and loop fasteners tend to couple together throughout their contacting surfaces and resist separation, it is relatively difficult to manually open them.

An additional object of the invention, therefore, is to provide a device using filamentary hook and loop fasteners to retain a reusable absorbant pad insert to a garment.

Another object is to provide in such a device a self-closing characteristics to protect the filamentary loops from lint while enabling an individual to easily manually separate the hook and loop fasteners and thereby release the pad.

DISCLOSURE OF INVENTION

A garment, which preferably is a diaper or diaper cover, is formed of a first piece of fabric having at one end a pair of arcuate, outwardly extending corners. Filamentary hook fastener strips on the extending corners are adapted to couple to a strip of filamentary loop fastener material at the opposite end of the garment when the garment is folded to be worn. Additional fabric carrying strips of filamentary loop material positioned at the corners of the garment to protectively self-close with and cover the filamentary hook fasteners during washing.

Preferably, the filamentary hook and protective filamentary loop strips are provided on opposite ends of a single, approximately eliptical, piece of fabric, folded at its center and attached thereat to each of the two extended corners of the garment. The protective loop strip is shorter than the filamentary hook strip, and is positioned adjacent the outer end of the fabric. This helps pivot the filamentary loop strip into contact with the filamentary hook to establish a "self-closing" characteristic. A bias strip on the edge of the fabric carrying the selfclosing filamentary strips prevents the edge from fraying and furthermore accentuates the self-closing characteristic of the strips by weighting the edge of the fabric base.

In another embodiment of the invention, filamentary loop and hook fastener strips are provided on corresponding central portions of a pair of fabric tabs. Each fabric tab has one end attached to a waist band or pants, and a region of the tabs between the fastener strips and belt establishes a "loop" when the tabs are closed. An absorbent pad, adapted to be retained to the body of the wearer, is provided with a continuous bias strip that extends along the edges of the pad and forms loops at the ends. The end loops of the absorbant pad are coupled to the loops formed by the two fabric tabs attached to the waist band or pants to retain the pad to the wearer.

In a further embodiment of the invention, a garment formed of a fluid absorbent fabric has an approximately rectangular configuration formed with opposite side openings to accommodate the legs of a wearer. Fabric tabs carrying filamentary hook and protective loop fastener strips extend outward from opposite sides of one end of of the garment. The tabs are bifurcated, to enable the garment to accommodate a wide range of waist and leg sizes of infant and adult wearers.

In each embodiment, the filamentary strips are stabilized by the fabric tabs upon which the strips are sewn. The trips thereby tend to resist warpage and deterioration when exposed to the high temperatures of commercial laundering.

Still other objects and advantages of the present invention will become readily apparent to those skilled in this art from the following detailed description, wherein we have shown and described only the preferred embodiments of the invention, simply by way of illustration of the best modes contemplated by us of carrying out our invention. As will be realized, the invention is capable of other and different embodiments, and it several details are capable of modification in various obvious respects, all without departing from the invention. Accordingly, the drawings and description are to be regarded as illustrative in nature, and not as restrictive.

BEST MODE FOR PRACTICING THE INVENTION

Figure 1:
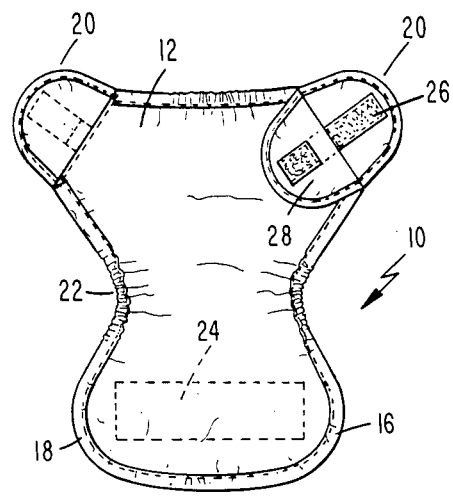
FIG. 1 is a view of a garment embodying filamentary hook and loop fasteners in accordance with one embodiment of the invention.
Figure 2:
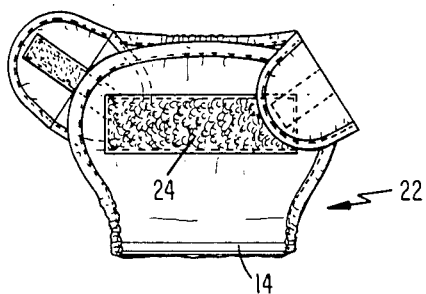
FIG. 2 is a view of the garment of FIG. 1, folded to be worn and secured by the fastener strips.

Referring to FIGS. 1 and 2, a diaper 10 constructed in accordance with the principles of the invention, comprises a fluid absorbant fabric 12, forming an inner layer of the diaper, and an outer, fluid resistant layer 14, held to layer 12 by a bias strip 16 on the edge of the diaper. Alternatively, the two layers 12, 14 may be secured together by folding the fluid resistant layer 14 over the edge of the absorbant layer 12, and stitching. In either case, the two layers are profiled, as shown in FIG. 1, with one end 18 adapted to rest on the stomach of an infant and an opposite end 20 adapted to cover the rear. Between the ends 18 and 20 of the diaper is a narrow, elastic region 22 adapted to accommodate the legs of the infant.

On the layer 14 of the diaper at end 18 is a strip of filamentary loop fastener material 24 such as a type made by Velcro Corporation and known as a Velcro R loop fastener strip. At each corner of the opposite end 20 of the diaper is a strip of filamentary hook fastener material 26 which is adapted to couple to the filamentary loop fastener strip 24 when the diaper is folded, as shown in FIG. 2, to be worn by an infant. It is clear from FIG. 2 that, with the legs of the infant extending outward from the diaper at regions 22, the filamentary hook fastener strip 26 at each corner of the diaper is coupled to the filamentary loop strip 24 at positions appropriate to create a snug, yet comfortable, fit at the waist of the infant.

Figure 3:
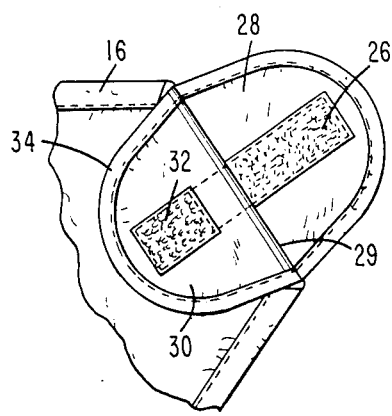
FIG. 3 is detailed view of the hook and protective loop filamentary fastener strips at one corner of the garment.

With reference to FIG. 3, the filamentary hook fastener strip 26 is on a fabric tab 28 having an arcuate shape, attached to and extending outward from each corner of the end portion 20 of the diaper 10. To ensure as much contact area between the filamentary hook fastener strip 26 on fabric base 28 and filamentary loop fastener strip 24 on the diaper at 18, the length of the strip 26 must be as long as possible, and may extend to the line of attachment 24 between tab 28 and the diaper, as shown in FIG. 3.

A second fabric base or tab 30 having an arcuate shape corresponding to the shape of tab 28 carries a strip of filamentary loop fastener material 32. The tab 30 is attached to the corner of the diaper 10 so as to be coextensive with tab 28. The length of the filamentary loop strip 32 is considerably less than the length of filamentary hook loop 26, and the strip 32 is positioned relatively near the outer end of the tab 30. The edge of the tab 30 as well as the edge of tab 28 is preferably covered by a bias strip 34.

Figure 5:
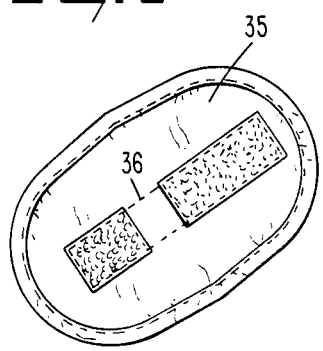
FIG. 5 is a view of an integral fabric base for the filamentary strips.
Figure 4A:
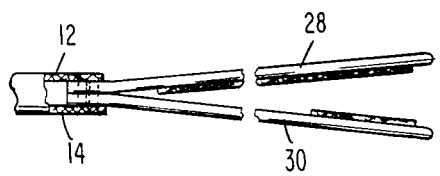
FIGS. 4 A–C are side views of three embodiments of filamentary fastener strips of FIG. 3.
Figure 4B:
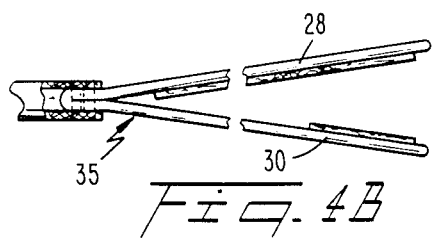
Figure 4C:
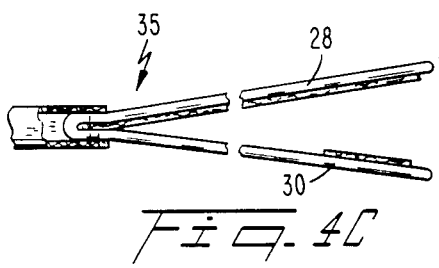

The tabs 28 and 30 may be constructed as separate pieces of fabric stitched between the fluid absorbant and fluid resistant layers 12 and 14 of the diaper, as shown in FIG. 4A. Preferably, however, the two tabs 28, 30 are formed of a single fabric base, having approximately an elliptical shape as shown in FIG. 5. The two strips 26 and 32 preferably are secured to the base by a single sewn stitch 36 in the locations shown in FIG. 3. The base 35 then is folded at its center and stitched between the diaper layers 12 and 14, with the longer strip 26 extending near but not between the layers, as shown in FIG. 4B, or alternatively sewn between the layers, as shown in FIG. 4C.

The tabs 28 and 30 significantly improve the ability of the garment to resist damage when the fasteners 26, 32 are exposed to vary high washing temperatures as is common in commercial laundries. Because the filamentary hook and loop fasteners 26 and 32 are sewn to extending fabric bases, heat that otherwise would be absorbed by only the strips is now spread over the fabric. Furthermore, any wrinkling of the strips 26 and 32 that has a tendency to occur during exposure to high washing temperatures is substantially reduced by the tabs 28 and 30 (or base 35) on which the strips are sewn. In this regard, it is important that the fabric forming tabs 28 and 30 and, in the embodiment of FIG. 5, base 35, be nonshrinking since the material forming the standard filamentary fastener strips 26, 32 (typically nylon) does not wrinkle; any shrinkage of the fabric would thus tend to cause warping of the tabs.

Another substantial advantage of the fastener configuration of FIGS. 3–5 over independent strips of filamentary material is in improved self-closing. As described in U.S. Pat. No. 4,537,591 to Coates, independent filamentary hook and loop fastener strips provided in face to face presentation to each other will tend to self-close to protect the filamentary hooks from accumulating lint during washing. This is caused in part by the rigidity of the nylon carrying the filamentary strip materials enabling the strips to pivot and by static electricity which provides mutual attraction between the strips. In the present invention, however, the self-closing characteristic is enhanced by positioning a relatively short filamentary loop strip 30 near the outer end of the tab 30, to shift the center of gravity of the tab toward the outer end. We have observed that the tendency of the strip 32 to pivot about the corner 24 of the diaper 10 into contact with strip 16 is significantly enhanced by the configuration and placement of strip 32 on tab 30 shown in FIG. 3. The tendency of the strips 26 and 32 to self-close is further enhanced by the bias strip 34 on the edges of the fabric tabs 28 and 30 or on the edge of the unitary fabric base 35 because the tabs are made more rigid and are weighted toward their edges. The strip 34 further "dresses" the edges of the tab 28, 30 and prevents fraying.

Figure 6:
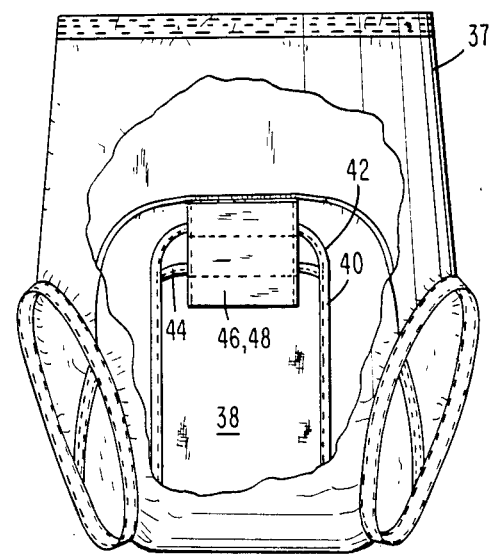
FIG. 6 is a view of pants having a pair of filamentary tabs, in accordance with another embodiment of the invention, for retaining the end loops of a novel absorbent pad.

FIGS. 6 and 7A–7C an adaptation of the filamentary strips and fabric tabs of FIGS. 1–4C for retention of an absorbant, reusable pad insert, within a pair of pants 37 that may be worn by an adult. In reference to FIG. 6, a fluid absorbant, elongated pad 38 has inner and outer fluid absorbant and resistant layers held together by a bias strip 40. The bias strip 40 preferably is a single strip on only the long sides of pad 38, extending beyond the ends of the pad to form a pair of closed loops 42 (only one loop is shown in FIG. 6). Additional strips of bias material 44 are on the ends of the pad 38 to dress the edges.

Figure 7A:
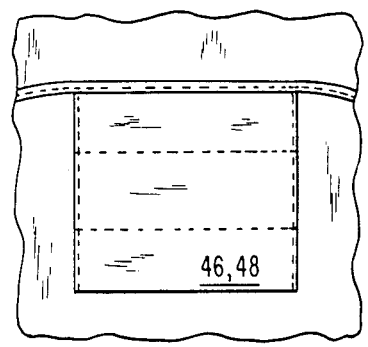
FIG. 7A is a front view of the fastener tabs of FIG. 6 closed.
Figure 7B:
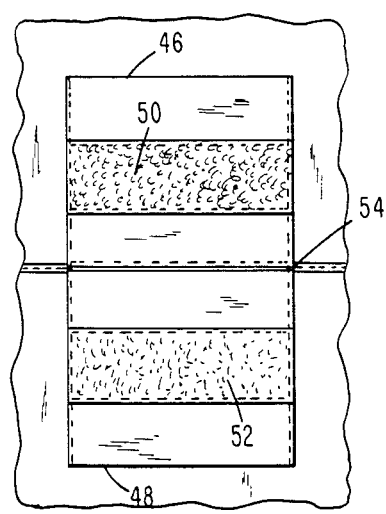
FIG. 7B is a front view of the fastener tabs of FIG. 6 open.
Figure 7C:
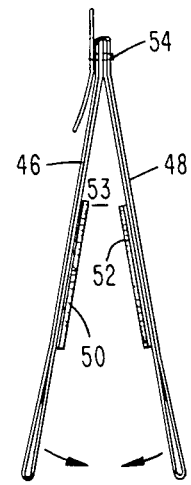
FIG. 7C is a side view of the fastener tabs of FIGS. 7A and 7B.

Stitched within the pants 37 at the front and rear, just below the waist, are pairs of tabs 46 and 48, best shown in FIG. 7C. Each tab is formed of a piece of shrink resistant fabric, folded back to form a double ply and sewn to the inner surface of the pants 37. A strip of filamentary loop material 50 is positioned on a central portion of tab 46, and similarly, a strip of filamentary loop material is in a corresponding position on tab 48. With reference to FIG. 7B, the strips 50 and 52 have a "horizontal" orientation; they span the width of each tab.

Between each strip 50, 52 and seam 54 is established a "loop" 53 that couples to the closed loop 42 of absorbant pad 38, shown in FIG. 6. Beneath each strip 50, 52 are portions of the tab 46, 48 that form "gripping ends" to enable the user to easily manually separate the tabs and remove the pad 38.

Figure 8:
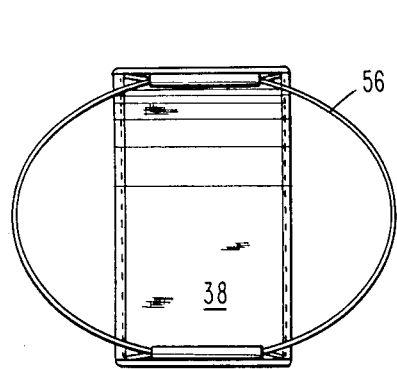
FIG. 8 is a top view of a waist belt and pair of fastener tabs carrying the absorbant pad of FIG. 6.
Figure 8A:
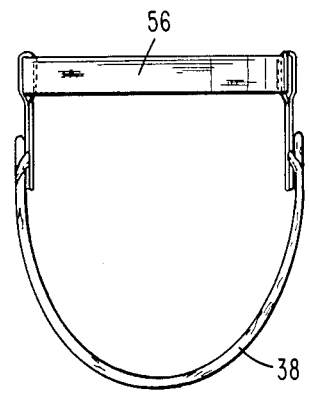
FIG. 8A is a side view of the waist belt an absorbant pad insert.
Figure 8B:
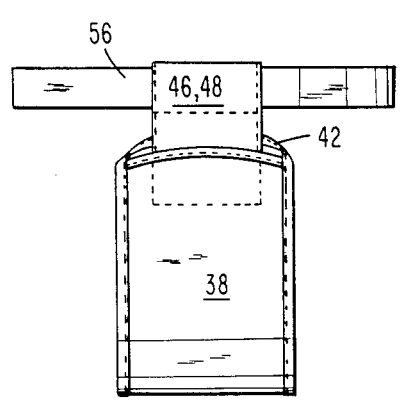
FIG. 8B is an end view of the assembly of FIG. 8.
Figure 8C:
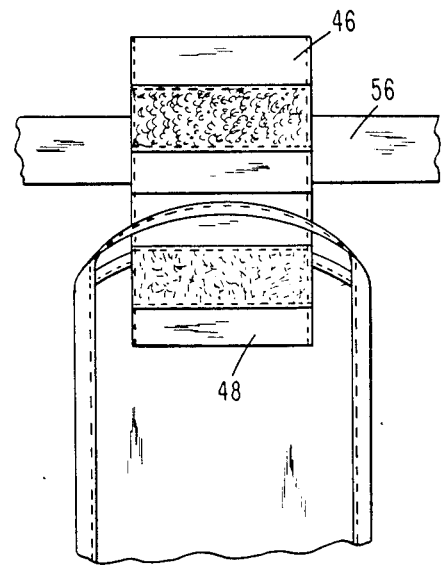
FIG. 8C is a detailed view of the waist band and absorbant pad insert with filamentary fastener tabs open to release the pad.

FIGS. 8–8C are a variation, wherein the tabs 46, 48 are sewn to a waist-hip belt 56, rather than to pants. FIG. 8B shows more clearly how the tabs 46, 48 interfit with loop 42 of pad 38. In FIG. 8C, the tabs 46, 48 have been manually separated to release the pad 38.

Figure 9:
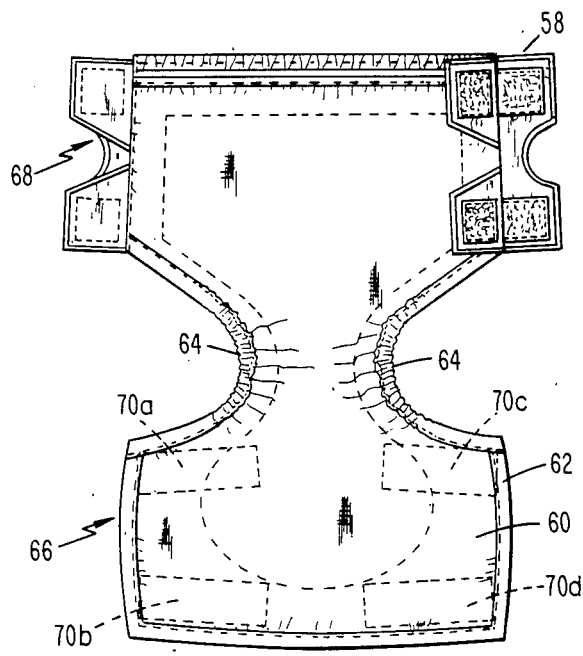
FIG. 9 is a view of a garment constructed in accordance with a third embodiment of the invention.
Figure 9B:
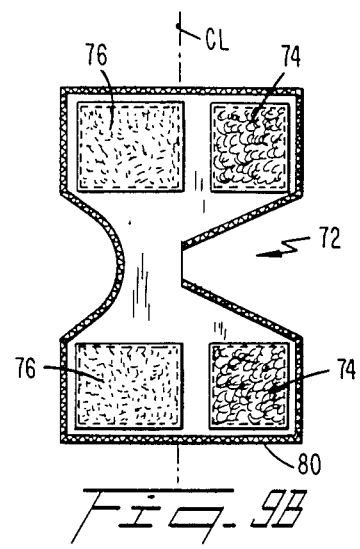
FIG. 9B is a view of a fabric base carrying pairs of filamentary hook and protective loop strips.
Figure 9A:
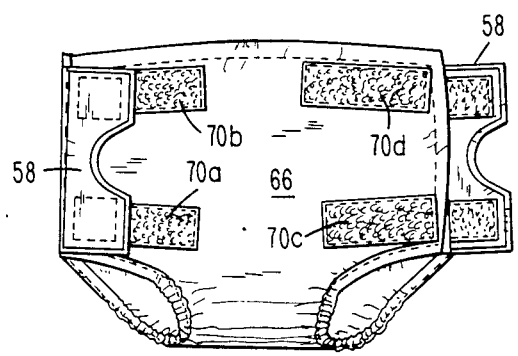
FIG. 9A is a view of the garment of FIG. 9, folded to be worn and secured with one set of filamentary fasteners.
Figure 9C:
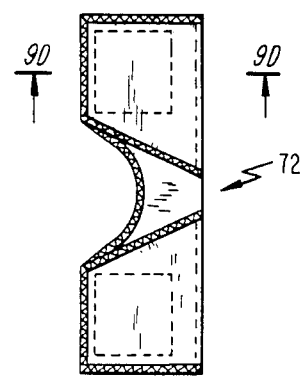
FIG. 9C is a view of the fabric base folded and attached at its center to one side of the garment.
Figure 9D:
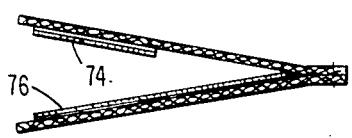
FIG. 9D is an end view of the fabric base, partially open to expose the filamentary hook and loop strips.

FIG. 9–9D are a further modification, wherein, fabric tabs 58 have configurations that are well adapted to improve the comfort and effectiveness of absorbant pants or diapers for adult wear, particularly significant in view of the growing need for quality geriatric care. The pants 60 (FIG. 9) to which the tabs 58 are attached comprises fluid absorbant and resistant layers sewn together at a bias strip or back-fold 62 along the edge of the pants. The layers have an approximately rectangular shape, with elastic leg openings formed at 64 between front 66 and rear 68 portions of the pants.

At the outer surface of front portion 66 of the pants, there are provided four strips of filamentary loop fastener 70a–70d. Strips 70a and 70d are on one side of the pants near the one leg and the waist whereas the strips 70c and 70d are in corresponding positions on the opposite side of the pants. This is to enable the pants to be adjusted to fit comfortably individuals having substantially different waist and leg sizes.

At the opposite end of the pants 60, each pair of tabs 58 is formed preferably by a fabric base 72 having a somewhat bifurcated configuration as shown in FIG. 9B. The base 72 is formed of a non-shrinking fabric onto which is sewn relatively short, filamentary loop fastener strips 74 and somewhat longer, filamentary hook fastener strips 76. At the region of the tab 72 between strips 74, there is a trapezoidal cutout that extends to the center CL of the tab. The strips 76 extend preferably to or substantially to the center CL. Thus, with the tab 72 is folded about center line CL as shown in FIG. 9C, and sewn to the sides of the pants as shown in FIG. 9, the strips 74 tend to self-close onto strips 76. The self-closing characteristic of the tab is optimized by the configuration of the tab 72, with the trapezoidal cutout mechanically decoupling the two strips 74 from each other. Further, the strips 74 being shorter than strips 76 and positioned on the tab to shift outward the center of gravity helps pivot the strips 74 about center line CL into contact with strips 76.

At the opposite end of tab 72, there is a semi-circular cutout between strips 76 enable the two strips to be separated somewhat from each other while forming a liquid barrier between the tabs to prevent leakage onto the stomach of the wearer. To prevent the edge of the tab 72 from fraying, the edge of the tab is finished by overedging 80, shown in FIG. 9B.

As shown in FIG. 9A, as the garment is folded to be worn, 72 are able to be positioned somewhat independently of each other on the four fastener strips 70a–70b on the front portion 66 of the garment. It is apparent that the pants can thus accommodate individuals having a wide variations of leg and waist sizes.

For the comfort of the wearer the strips 70a–70d on portions 66 are inset from the side edges of the pants by a distance sufficient to ensure that the filamentary hook fasteners 76 do not extend beyond the side of the pants into contact with the skin of the wearer. The minimum distance between each fastener 70a–70d and the side edge of the pants should, therefore, be no smaller than the length of the filamentary hook fastener strips 76.

In this disclosure, there is shown and described only the preferred embodiments of the invention, but, as aforementioned, it is to be understood that the invention is capable of use in various other combinations and environments and is capable of changes and modifications within the scope of the inventive concept as expressed herein.

What is claimed is:

1. A garment, comprising:
   a first piece of fabric;
   a first fastener means attached to and extending outward from the first piece of fabric, said first fastener means comprising a second piece of fabric having one end attached to the first piece, a first filamentary fastener provided on a portion of said second piece of fabric;
   a second fastener means comprising a second, complementary filamentary fastener on a surface of said first piece of fabric and adapted to be coupled to the first fastener means when the first fabric is folded to be worn; and
   cover means comprising a third piece of fabric attached only at one end to and extending outward from the first piece of fabric and substantially coextensive with the second piece of fabric, a third, complementary filamentary fastener material provided on a portion of the third piece of fabric face to face and coextensive with at least a portion of the first filamentary fastener;
   the first and third filamentary fasteners thereby tending to self-close to each other during washing.

2. The garment of claim 1, wherein said first fastener means comprises filamentary hooks and said second and third fastener means comprises filamentary loops.

3. The garment of claim 1, including a bias strip on an edge of at least one of said second and third pieces of fabric.

4. The garment of claim 1, wherein said second and third pieces of fabric have an arcuate shape.

5. The garment of claim 2, wherein said second and third pieces of fabric are formed of a single, approximately elliptical, piece of fabric, folded at its center and attached thereat to the first piece of fabric.

6. The garment of claim 1, wherein the first and third filamentary fasteners are strips of filamentary fastener material, the length of the strip of the first filamentary fastener being greater than that of the third filamentary fastener.

7. The garment of claim 6, wherein the strip of the third filamentary fastener is positioned adjacent a free end of the third piece of fabric.

8. A garment formed of a first piece of fabric profiled to fit a mid-section of a wearer, opposite corners of one end of said first piece of fabric forming arcuate extensions, each extension carrying a first strip of a first type filamentary fastener material; a second strip of a second type filamentary fastener material complimentary to the first type provided on a surface of the garment remote from said opposite corners and adapted to be coupled to the first strips of fastener material when the garment is worn; and a protective cover at each of said opposite corners, each said cover being formed of an additional piece of fabric having only one end attached to the first piece of fabric and an opposite end free, and being substantially coextensive with its corresponding arcuate extension, a portion of each said cover having adjacent its free end a third strip of the complementary type filamentary fastener material face to face and at least partially coextensive with said first strip, the first and third strips of filamentary fastener material thereby tending to self-close to each other during washing.

9. The garment of claim 8, wherein said first type filamentary material comprises filamentary hooks and the complimentary type filamentary material comprises filamentary loops.

10. The garment of claim 8, including a bias strip on an edge of said cover.

11. The garment of claim 1, wherein a fluid resistant layer is attached to said first piece of fabric and said second piece of fabric is retained to said garment between said first piece of fabric and fluid resistant layer.

12. The garment of claim 11, wherein on end of said first strip of filamentary fastener material on said second piece of fabric is retained between said first piece of fabric and fluid resistant layer, and the third strip of complementary filamentary fastener material is positioned on an outer end portion of said third piece of fabric.

13. The garment of claim 12, wherein said third piece of fabric is retained with said second piece of fabric between said first piece of fabric and said fluid resistant layer.

14. The garment of claim 13, wherein each said extension and its corresponding cover are formed of a single piece of fabric folded at its center and retained thereat between said first fabric and fluid resistant layer.

15. The garment of claim 5, wherein said first and second filamentary material strips are attached to the single piece of fabric by a continuous stitch.

16. A garment formed of a first fabric having an approximately rectangular configuration with openings formed on opposite sides thereof to accommodate the legs of a wearer, front and rear portions of the garment established respectively on opposite ends of the leg openings;
   first strip means of one type of filamentary fastener material on an outer surface of the front portion of the garment;
   a pair of second strips of a complimentary type of filamentary fastener material attached to and extending laterally outward from a side of the rear portion of the garment, the pair of second strips spaced from each other along the side of the garment and adapted to be coupled to said first strip means with the garment wrapped around the body of the wearer, said pair of second fastener strips provided on a first fabric base;
   said first fabric base having a substantially rectangular configuration with a portion between the pair of second filamentary fastener strips open, said open portion extending along only a portion of the width of the first fabric base; and
   cover means comprising third, complimentary filamentary fastener strips, mounted on a second fabric base coextensive with the first fabric base with the third fastener strips and facing the second fastener strips, an opening formed in the second fabric base between the third fastener strips and extending along substantially the width of the second fabric, the second and third fastener strips thereby tending to self-close for protection of the second fastener strips during washing.

17. The garment of claim 1, wherein said first and second fabric bases are formed by a common fabric base, folded at approximately its center and attached thereat to said first fabric.

18. The garment of claim 17, including an overedging on an edge of said common fabric base.

19. The garment of claim 17, wherein the length of the third strips is less than the length of the second strips.

20. The garment of claim 17, wherein the length of the second strips is less than a distance between the first strips and an adjacent side of the garment.

* * * * *